Figures 1, 3:
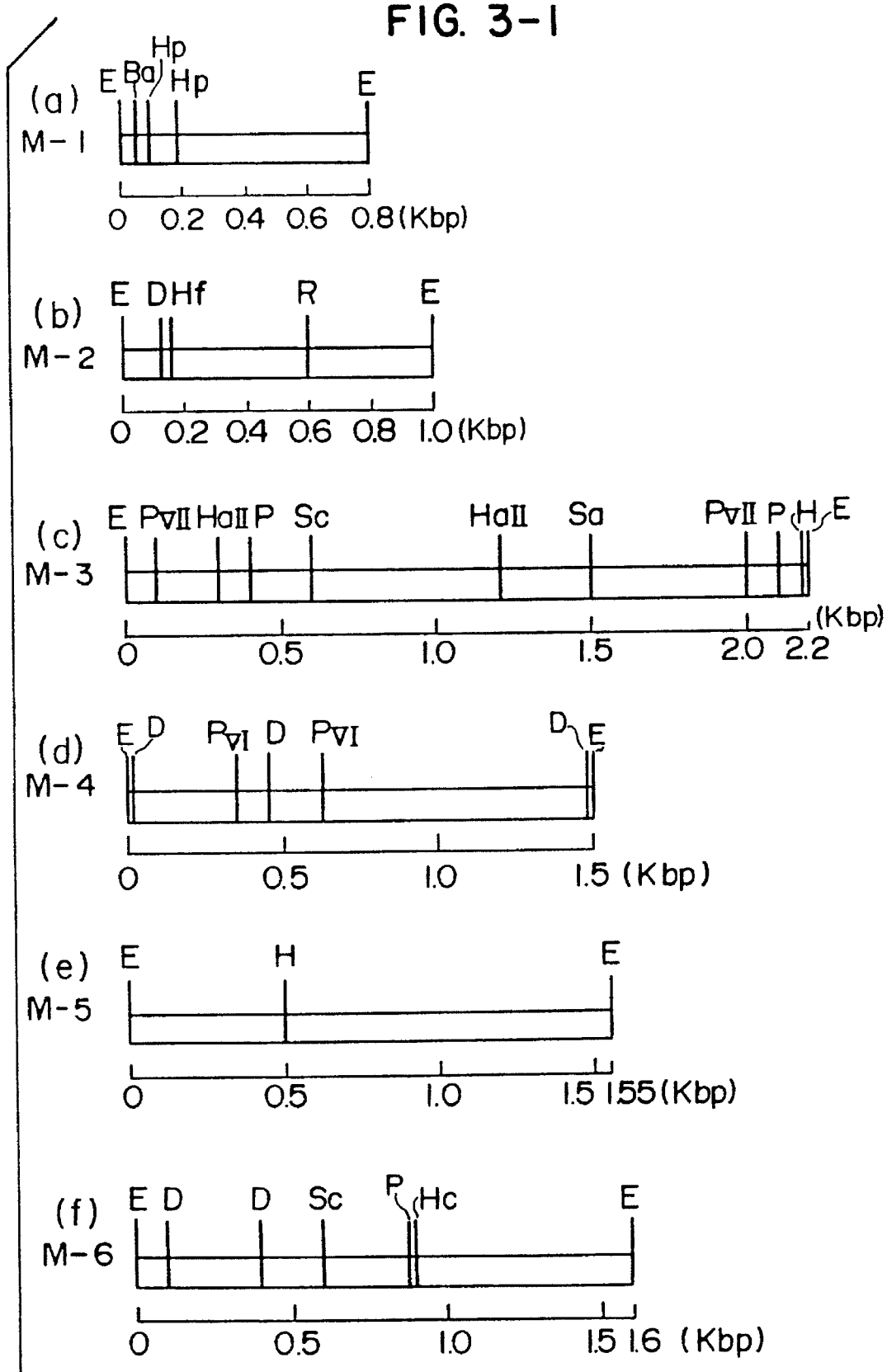

United States Patent [19]

Kodama et al.

[11] Patent Number: 5,621,076

[45] Date of Patent: *Apr. 15, 1997

[54] POULTRY MYCOPLASMA ANTIGENS AND RECOMBINANT VECTORS CONTAINING THE GENE AS WELL AS DIAGNOSTICS AND VACCINES UTILIZING THE SAME

[75] Inventors: Kazumi Kodama, Yokohama; Shuji Saito; Noboru Yanagida, both of Kawasaki; Kouichi Kamogawa, Yokohama; Yoshikazu Iritani, Kyoto; Shigemi Aoyama, Shiga-ken, all of Japan

[73] Assignees: Nippon Zeon Co., Ltd., Tokyo; Shionogi & Co., Ltd., Osaka, both of Japan

[ * ] Notice: The term of this patent shall not extend beyond the expiration date of Pat. No. 5,489,430.

[21] Appl. No.: 299,662

[22] Filed: Sep. 2, 1994

Related U.S. Application Data

[63] Continuation of Ser. No. 888,320, May 27, 1992, abandoned, which is a continuation of Ser. No. 359,779, May 31, 1989, abandoned.

[30] Foreign Application Priority Data

Jun. 2, 1988 [JP] Japan .................................. 63-136343

[51] Int. Cl.⁶ .................................................. C07K 14/30
[52] U.S. Cl. .................. 530/350; 424/190.1; 424/192.1; 424/264.1; 530/395
[58] Field of Search .............................. 424/163.1, 164.1, 424/234.1, 264.1, 190.1, 192.1; 435/69.7, 172.3, 252.33, 320.1, 252.3; 530/388.4, 350, 389.5, 395

[56] References Cited

U.S. PATENT DOCUMENTS 5,064,647  11/1991  Storm ........................................ 424/92
5,196,514  3/1993  Avakian .................................. 530/350
5,489,430  2/1996  Saito et al. ............................. 424/190.1

FOREIGN PATENT DOCUMENTS 0196215  1/1986  European Pat. Off. .................. 424/92
8800977  2/1988  WIPO ..................................... 424/92

OTHER PUBLICATIONS

Adler et al, "Immunization Against *Mycoplasma gallisepticum*," *Avian Diseases* 14:763–769, 1970.

Chemical Abstracts, vol. 108, No. 21, 23rd May 1988, p. 528, abstract No. 184793p, Columbus, Ohio, US; L.D. Bradley et al.: "Identification of species–specific and inter–species–specific polypeptides of *Mycoplasma gallisepticum* and *Mycoplasma synoviae*" & Am. J. Vet. Res 1988, 49(4), 511–15 *Abstract*.

Birnboim, H.C., et al, "A rapid alkaline extraction procedure for screening recombinant plasmid DNA," *Nucleic Acids Research*, vol. 7, No. 6 (1979), pp. 1513–1523.

Shirakawa, M., et al, "Plasmid vectors designed for high–efficiency expression controlled by the portable recA promoter–operator of *Escherichia coli*," *Gene*, No. 28 (1984), pp. 127–132.

Sanger, F., et al, "DNA sequencing with chain–termination inhibitors," *Proc. Natl. Acad. Sci. USA*, vol. 74, No. 12 (Dec. 1977), pp.5463–5467.

Noboru Y., et al, "Specific Excretion of *Serratia marcescens* Protease through the Outer Membrane of *Escherichia coli*," *Journal of Bacteriology*, vol. 166, No. 3 (Jun. 1986), pp. 937–944.

Primary Examiner—Robert D. Budens
Attorney, Agent, or Firm—Nikaido, Marmelstein, Murray & Oram LLP

[57] ABSTRACT

Antigen proteins of *Mycoplasma gallisepticum*, genes encoding the antigen protein, recombinant vectors integrated with the gene and hosts transformed with the vector are provided. Diagnostics and vaccine using the antigen protein produced by such hosts are effective for poultry, especially chicken infected with *Mycoplasma gallisepticum*. Vaccination can maintain poultry free of *Mycoplasma gallisepticum* infection.

9 Claims, 17 Drawing Sheets

FIG.I(a)-I

5'

TGT ATG TCT ATT ACT AAA AAA GAC GCA AAC CCA AAT AAT GGC CAA ACC CAA TTA
Cys Met Ser Ile Thr Lys Lys Asp Ala Asn Pro Asn Asn Gly Gln Thr Gln Leu
                    27                                              54

CAA GCA GCG CGA ATG GAG TTA ACT GAT CTA ATC AAT GCT AAA GCA AGG ACA TTA
Gln Ala Ala Arg Met Glu Leu Thr Asp Leu Ile Asn Ala Lys Ala Arg Thr Leu
                    81                                              108

GCT TCA CTA CAA GAC TAT GCT AAG ATT GAA GCT AGT TTA TCA TCT GCT TAT AGT
Ala Ser Leu Gln Asp Tyr Ala Lys Ile Glu Ala Ser Leu Ser Ser Ala Tyr Ser
                    135                                             162

GAA GCT GAA ACA GTT AAC AAT AAC CTT AAT GCA ACA CTA GAA CAA CTA AAA ATG
Glu Ala Glu Thr Val Asn Asn Asn Leu Asn Ala Thr Leu Glu Gln Leu Lys Met
                    189                                             216

GCT AAA ACT AAT TTA GAA TCA GCC ATC AAC CAA GCT AAT ACG GAT AAA ACG ACT
Ala Lys Thr Asn Leu Glu Ser Ala Ile Asn Gln Ala Asn Thr Asp Lys Thr Thr
                    243                                             270

TTT GAT AAT GAA CAT CCA AAT TTA GTT GAA GCA TAC AAA GCA CTA AAA ACC ACT
Phe Asp Asn Glu His Pro Asn Leu Val Glu Ala Tyr Lys Ala Leu Lys Thr Thr
                    297                                             324

TTA GAA CAA CGT GCT ACT AAC CTT GAA GGT TTA GCT TCA ACT GCT TAT AAT CAG
Leu Glu Gln Arg Ala Thr Asn Leu Glu Gly Leu Ala Ser Thr Ala Tyr Asn Gln
                    351                                             378

FIG.1(a)-2

```
       ATT CGT AAT AAT TTA GTG GAT CTA TAC AAT AAT GCT AGT AGT TTA ATA ACT AAA  432
       Ile Arg Asn Asn Leu Val Asp Leu Tyr Asn Asn Ala Ser Ser Leu Ile Thr Lys

ACA CTA GAT CCA CTA AAT GGG GGA ATG CTT TTA GAT TCT AAT GAG ATT ACT ACA  486
       Thr Leu Asp Pro Leu Asn Gly Gly Met Leu Leu Asp Ser Asn Glu Ile Thr Thr

GTT AAT CGG AAT ATT AAT ACG TTA TCA ACT ATT AAT GAA CAA AAG ACT AAT      540
       Val Asn Arg Asn Ile Asn Thr Leu Ser Thr Ile Asn Glu Gln Lys Thr Asn

GCT GAT GCA TTA TCT AAT AGT TTT ATT AAA AAA GTG ATT CAA AAT AAT GAA TTT  594
       Ala Asp Ala Leu Ser Asn Ser Phe Ile Lys Lys Val Ile Gln Asn Asn Glu Gln

AGT TTT GTA GGG ACT TTT ACA AAC GCT AAT GTT CAA CCT TCA AAC TAC AGT TTT  648
       Ser Phe Val Gly Thr Phe Thr Asn Ala Asn Val Gln Pro Ser Asn Tyr Ser Phe

GTT GCT TTT AGT GCT GAT GTA ACA CCC GTC AAT TAT AAA TAT GCA AGA AGA ACG  702
       Val Ala Phe Ser Ala Asp Val Thr Pro Val Asn Tyr Lys Tyr Ala Arg Arg Thr

705
GTTTGA                                                                        708
Val
```

FIG. 1(b)

```
      EcoRI           15                30              43              53              63
5' GAA TTC GAC AGC TTG TTG TTG GCC GGG GTT TAG ACGCATAGGT GTATTGCTCA ATCTTCGAAC
   Glu Phe Asp Ser Leu Leu Leu Ala Gly Val stop
           73          83            93           103            113            123             133
   GGGGGGAGGA TTGTAGCAGA ATCGCATTTG AATGTGACCG CGTGTAAGCC GCTAACCGGT TGCTGCGGAT
           143            153           163    HinfI
   GTTTAAATCA GAGAGACGAG ACCGAATGAG TCATCGTGA
```

FIG.1(c)

```
                         27                                                   54
GAA TTC CGC GCC TGT ACT TCA GCA ACT ACA CCA ACT CCA AAC CCT GAA CCG AAG
Glu Phe Arg Ala Cys Thr Ser Ala Thr Thr Pro Thr Pro Asn Pro Glu Pro Lys 81                                                  108
CCA AAG CCT GAA CCA AAT CCA AAC CCT GAA CCA AAA CCA GAT CCA ATG CCA AAC
Pro Lys Pro Glu Pro Asn Pro Asn Pro Glu Pro Lys Pro Asp Pro Met Pro Asn 135                                                  162
CCT TCT AGT GGT GGT ATG AAT GGC GGA GAT ACT AAT CCA GGA AAT AGC GGA GGA
Pro Ser Ser Gly Gly Met Asn Gly Gly Asp Thr Asn Pro Gly Asn Ser Gly Gly 189                                                  216
ATG GAT AAT TCT GCT CAA CAA TTA TCA GCT GCT AAA ACA GCT TTA ACT AAT TTA
Met Asp Asn Ser Ala Gln Gln Leu Ser Ala Ala Lys Thr Ala Leu Thr Asn Leu 243                                                  270
TTA AAT GGT CAA ACT GAA AAA GTT GGA TTA TAT AAT GAC TAT GCA AAA ATC AAA
Leu Asn Gly Gln Thr Glu Lys Val Gly Leu Tyr Asn Asp Tyr Ala Lys Ile Lys 297                                                  324
GAC GAT TTA GTA AAA GCT TAC ACT GCA GCT AAA GAA ATT TCA GAT AAA TCT GAT
Asp Asp Leu Val Lys Ala Tyr Thr Ala Ala Lys Glu Ile Ser Asp Lys Ser Asp 351                                                  378
GCA ACT TTA CAA GAA GTA AAT AAT GCT AAA ACA ACA TTA GAA ACT GCA ATA ACT
Ala Thr Leu Gln Glu Val Asn Asn Ala Lys Thr Thr Leu Glu Thr Ala Ile Thr 405                                                  432
ACT GCT GCA AGT TCA AAA ACT AGT TTT GAT GAA AAA AAT CCT GAA TTA ATC AAA
Thr Ala Ala Ser Ser Lys Thr Ser Phe Asp Glu Lys Asn Pro Glu Leu Ile Lys 459                                                  486
GCA TAT AAT GCT TTA AAA CAA ACG ATT ACT TCT GAA GAA ATG CAA TTA AAT CAG
Ala Tyr Asn Ala Leu Lys Gln Thr Ile Thr Ser Glu Glu Met Gln Leu Asn Gln 513                                                  540
TTG AAG GAT GCT AAT TTT GAA ACG ATT AAA AAC CAT ATA TCA AAT CTT TAT AAA
Leu Lys Asp Ala Asn Phe Glu Thr Ile Lys Asn His Ile Ser Asn Leu Tyr Lys 567                                                  594
CAA GGA AAA GAT ATC ATA ACA GCA ACA TTA GAC CCA ACA ACA GGA GAT GGT CCT
Gln Gly Lys Asp Ile Ile Thr Ala Thr Leu Asp Pro Thr Thr Gly Asp Gly Pro 621                                                  648
CAA GCT ATG GTA GTT AAT CAA GCC AAT GAA GCA ATT GTG AAT GCA ACC TCA AAA
Gln Ala Met Val Val Asn Gln Ala Asn Glu Ala Ile Val Asn Ala Thr Ser Lys 675                                                  702
CTT GAG GAT TGA AAA ACT AAT GCC ACT AAT TTA GCT ACC AGG TTT GTA AAG CAA
Leu Glu Asp  .
```

FIG. I(d)

```
                              27                                              54
GAA TTC CGC GCT AAA TAT ACA TTA ACA TTT GAT TAT TAT GGC CCA CAA ACT GGT
Glu Phe Arg Ala Lys Tyr Thr Leu Thr Phe Asp Tyr Tyr Gly Pro Gln Thr Gly 81                                             108
TAT TTA TAT TTT CCT TAT AAG TTA GTT AAA GAT GCC GAT AAA AAT AAT ATC GGG
Tyr Leu Tyr Phe Pro Tyr Lys Leu Val Lys Asp Ala Asp Lys Asn Asn Ile Gly 135                                             162
CTT CAA TAT AAA TTA AAC GAC GGT AAT TTT GAG CAA ATC AAT TTT GCG CAA ACA
Leu Gln Tyr Lys Leu Asn Asp Gly Asn Phe Glu Gln Ile Asn Phe Ala Gln Thr 189                                             216
CAA CCT GTT GAA TCA GAA TCA GCA GCA ACT GAA CCG GCT AGA TCA ACT ATG CCT
Gln Pro Val Glu Ser Glu Ser Ala Ala Thr Glu Pro Ala Arg Ser Thr Met Pro 243                                             270
CAA ACA GCA CCA GAA AAT CAA ACT TCT GAA GAA AAT ATG ACT GTT GCT AGC CAA
Gln Thr Ala Pro Glu Asn Gln Thr Ser Glu Glu Asn Met Thr Val Ala Ser Gln 297                                             324
TTA AAT CCA ACT CCT ACA GTA AGT GAT ATT AAT GTT GCT AAA GTG ACT TTA TCT
Leu Asn Pro Thr Pro Thr Val Ser Asp Ile Asn Val Ala Lys Val Thr Leu Ser 351                                             378
AAT TTA AAG TTT GGT TCT AAC ACA ATT GAA TTT AGT GTT CCA ACG GGT GAA GGT
Asn Leu Lys Phe Gly Ser Asn Thr Ile Glu Phe Ser Val Pro Thr Gly Glu Gly 405                                             432
GAA ATG TCT AAA GTC GCT CCA ATG ATT GGG AAC ATG TAT TTA ACT TCA TCT GAT
Glu Met Ser Lys Val Ala Pro Met Ile Gly Asn Met Tyr Leu Thr Ser Ser Asp 459                                             486
AGC GAT GTT AAT AAA AAC AAG ATT TAT GAT GAT CTT TTT GGA AAT AAT TCA GTT
Ser Asp Val Asn Lys Asn Lys Ile Tyr Asp Asp Leu Phe Gly Asn Asn Ser Val 513                                             540
CAA CAA GAT AAT CAA ACA GCT GTT ACA GTT GAT TTA TTA AAA GGT TAT AGT CTT
Gln Gln Asp Asn Gln Thr Ala Val Thr Val Asp Leu Leu Lys Gly Tyr Ser Leu 567                                             594
GCA ACT AGT TGA AGA ACA TAT ATT CGT CAA TTT ACT GGT TTA ACA GGT AAT GGC
Ala Thr Ser  .
```

FIG. I(e)

```
                             27                                                   54
GAA TTC CGC GGC GCG GAA TCT CAA GAA AAA CCA AGA CAA CCA GCA AAC TTA GCT
Glu Phe Arg Gly Ala Glu Ser Gln Glu Lys Pro Arg Gln Pro Ala Asn Leu Ala 81                                                  108
ACT TTA AAA ACT GAT ATT GAT GAC AAG ATG TCA GAT GCA ATT GGG GAG TTT ATT
Thr Leu Lys Thr Asp Ile Asp Asp Lys Met Ser Asp Ala Ile Gly Glu Phe Ile 135                                                  162
CAA GCG ATC TTT TTA GGT AAA GAT AAT CTG ATC GAT CAA AAA ATT GCA GCG ATT
Gln Ala Ile Phe Leu Gly Lys Asp Asn Leu Ile Asp Gln Lys Ile Ala Ala Ile 189                                                  216
CAA AAT CAA AGT GAT CTA AGT TTT GAA GAG AAG TTT AAT AAA ACC CTT TAT TAT
Gln Asn Gln Ser Asp Leu Ser Phe Glu Glu Lys Phe Asn Lys Thr Leu Tyr Tyr 243                                                  270
TCT CAG ATC AAA GCA ATC TTT GCT AAG AAT CAA AAT GAG ATT AAA ACT AGC CCT
Ser Gln Ile Lys Ala Ile Phe Ala Lys Asn Gln Asn Glu Ile Lys Thr Ser Pro 297                                                  324
TCA AAA TTT GGT TTA GAT ATC GTT TAT CCT TAT GTG CTT TCA GCT AAT GCT GAA
Ser Lys Phe Gly Leu Asp Ile Val Tyr Pro Tyr Val Leu Ser Ala Asn Ala Glu 351                                                  378
TTT AAT AAA GGT ACG ATC GTA TTT AAT AAC AAA ACT TAT GAA AAT AAG ATT TGG
Phe Asn Lys Gly Thr Ile Val Phe Asn Asn Lys Thr Tyr Glu Asn Lys Ile Trp 405                                                  432
GGT AAT ACG GAT ACT ACC AAC TAT AAA AAA GAA GTT ACT GGT GAA GGA AAC TCA
Gly Asn Thr Asp Thr Thr Asn Tyr Lys Lys Glu Val Thr Gly Glu Gly Asn Ser 459                                                  486
ATT ACA CCA AAT GCA GAT CCA CAA AAA GCT AAA GTA CAA AAT ACT ACT TCA GAT
Ile Thr Pro Asn Ala Asp Pro Gln Lys Ala Lys Val Gln Asn Thr Thr Ser Asp

513
GAA GAA GGT AAG AAC GTT TTA AAA ACT TAC TTT AAT GCT TTA AAA CA
Glu Glu Gly Lys Asn Val Leu Lys Thr Tyr Phe Asn Ala Leu Lys
```

FIG.1(f)-1

```
                                                                                        54
GAA TTC AAC GGC GAT GCT CTC TTC CAA CAG GCG CGT TCC GGC GAT GCA CAC
Glu Phe Asn Gly Asp Ala Leu Phe Gln Gln Ala Arg Ser Gly Asp Ala His
                27

108
CTG TCC CTG GTT GTA GAA AAT GCC TGC TGC GGT GGC GCT TGC CGC CTG TTG CAA
Leu Ser Leu Val Val Glu Asn Ala Cys Cys Gly Gly Ala Cys Arg Leu Leu Gln
                81

162
ATC CGG GCA GTC AGC GAA AAC GAT GTT GGC GCT TTT GCC CGC TTC CAA CCA
Ile Arg Ala Val Ser Glu Asn Asp Val Gly Ala Phe Ala Arg Phe Gln Pro
               135

216
GAC GCG TTT CAT GTT GCT GTC GCC CGC ATC TTT CAG CAG CTG TTT CCC GGT ACG
Asp Ala Phe His Val Ala Val Ala Arg Ile Phe Gln Gln Leu Phe Pro Gly Thr
               189

270
GTT GAA CCG GTA AAG GAA TGG CGT CGA TAT TAT GAC GCG ACA GCG CCT GCC
Val Glu Pro Val Lys Glu Trp Arg Arg Tyr Tyr Asp Ala Thr Ala Pro Ala
               243

324
CGG CTT CAT GAC CAA AAC CCG TCA CCC ACG TTC AAC ACA CCA TCC GGC AAG CCT
Arg Leu His Asp Gln Asn Pro Ser Pro Thr Phe Asn Thr Pro Ser Gly Lys Pro
               297

378
GCT TCT TTC GCC AGC CCC GCG AGA CGA ATC GCA CTG AGC GGT GAT TTT TCA GAC
Ala Ser Phe Ala Ser Pro Ala Arg Arg Ile Ala Leu Ser Gly Asp Phe Ser Asp
               351

432
GGT TTT AGA ATC ACG CTG TTT CCC GCC GCC AGC GCC GGG CCG AGT TTC CAG CAA
Gly Phe Arg Ile Thr Leu Phe Pro Ala Ala Ser Ala Gly Pro Ser Phe Gln Gln
               405

486
GTC AGC AAC AGC GGG AAG TTC CAC ACG ATG GCG GCA ATC ACG CCG ACC GGT
Val Ser Asn Ser Gly Lys Phe His Thr Met Ala Ala Ile Thr Pro Thr Gly
               459
```

FIG.1(f)-2

```
    TCA CGC ACG ATC ATC GCC ACT CAT GGC TAC TGG TGG TCG CCA CTT CGC CAT ACA  540
    Ser Arg Thr Ile Ile Ala Thr His Gly Tyr Trp Trp Ser Pro Leu Arg His Thr

513
    CTT TGT CGA TCG CTT CGG CGT ACC ACG AAT GGC GCC CGC GCC GGG AAT ATC  594
    Leu Cys Arg Ser Leu Arg Arg Thr Thr Asn Gly Ala Arg Ala Gly Asn Ile

567
    ATC ACG CAG ACT GTG ACG AAT CGG TTT GCC GGT GTC GAG AGT TTC CAG AGT GCC  648
    Ile Thr Gln Thr Val Thr Asn Arg Phe Ala Gly Val Glu Ser Phe Gln Ser Ala

621
    AGC TCT TCG GCG TGG GCT TCC ATT AAA TCG GCG AGT TTA TTC AGT ACC GCT TTA  702
    Ser Ser Ser Ala Trp Ala Ser Ile Lys Ser Ala Ser Leu Phe Ser Thr Ala Leu

675
    CGT TTA GCC GGA GAA GAG AGT GAC CAG CCG TCA AAT ACG CCG CGT GCT  756
    Arg Leu Ala Gly Glu Glu Ser Asp Gln Pro Arg Ser Asn Thr Pro Arg Ala

729
    GCG CTC ATC GCA CGG TCG ATA TCG ACG GGA TCA ACG CTC TTG CCG CGG GCA ATT TTC GCC AGC  810
    Ala Leu Ile Ala Arg Ser Ile Ser Thr Leu Leu Pro Arg Ala Ile Phe Ala Ser

783
    GGT GCC TGG GTG ACC GGA TCA ACG GTT TCA AAG GTT TCA TTT TCC GCC GCA GCA  864
    Gly Ala Trp Val Thr Gly Ser Thr Val Ser Lys Val Ser Phe Ser Ala Ala Ala

837
    GTA TAT TCA CCG TTA ATA AAT AAG CGG TTT TCA ATG GCG AGA CTT AAC GCT TTA  918
    Val Tyr Ser Pro Leu Ile Asn Lys Arg Phe Ser Met Ala Arg Leu Asn Ala Leu

891
    TCC TGC CAG TAA GCC AGA TGA TGA AAA TTC ATT ATG ACT CCT GTT TCA CGT CTA  972
    Ser Cys Gln

945
```

FIG. 2(a)

```
                                                                    27                                          54
TTA GTC ATC TTT TAA GAT ATA AAT ATA TCT TAA TAT TCT ATG AAT AAG AAA AGA
                                                        Met Asn Lys Lys Arg 81                                                                                          108
ATC ATC TTA AAG ACT ATT AGT TTG TTA GGT ACA ACA TCC TTT CTT AGC ATT GGG
Ile Ile Leu Lys Thr Ile Ser Leu Leu Gly Thr Thr Ser Phe Leu Ser Ile Gly 135                                                                                         162
ATT TCT AGC TGT ATG TCT ATT ACT AAA AAA GAC GCA AAC CCA AAT AAT GGC CAA
Ile Ser Ser Cys Met Ser Ile Thr Lys Lys Asp Ala Asn Pro Asn Asn Gly Gln 189                                                                                         216
ACC CAA TTA CAA GCA GCG CGA ATG GAG TTA ACT GAT CTA ATC AAT GCT AAA GCA
Thr Gln Leu Gln Ala Ala Arg Met Glu Leu Thr Asp Leu Ile Asn Ala Lys Ala 243                                                                                         270
AGG ACA TTA GCT TCA CTA CAA GAC TAT GCT AAG ATT GAA GCT AGT TTA TCA TCT
Arg Thr Leu Ala Ser Leu Gln Asp Tyr Ala Lys Ile Glu Ala Ser Leu Ser Ser 297                                                                                         324
GCT TAT AGT GAA GCT GAA ACA GTT AAC AAT CTT AAT GCA ACA CTA GAA CAA
Ala Tyr Ser Glu Ala Glu Thr Val Asn Asn Leu Asn Ala Thr Leu Glu Gln 351                                                                                         378
CTA AAA ATG GCT AAA ACT AAT TTA GAA TCA GCC ATC AAC CAA GCT AAT ACG GAT
Leu Lys Met Ala Lys Thr Asn Leu Glu Ser Ala Ile Asn Gln Ala Asn Thr Asp 405                                                                                         432
AAA ACG ACT TTT GAT AAT GAA CAT CCA AAT TTA GTT GAA GCA TAC AAA GCA CTA
Lys Thr Thr Phe Asp Asn Glu His Pro Asn Leu Val Glu Ala Tyr Lys Ala Leu
```

FIG. 2(b)

```
                                                                         486
     459                                                                 GCT
AAA ACC ACT TTA GAA CAA CGT GCT ACT AAC CTT GAA GGT TTA GCT TCA ACT GCT
Lys Thr Thr Leu Glu Gln Arg Ala Thr Asn Leu Glu Gly Leu Ala Ser Thr Ala 540
     513                                                                 TTA
TAT AAT CAG ATT CGT AAT AAT TTA GTG GAT CTA TAC AAT AAT GCT AGT AGT TTA
Tyr Asn Gln Ile Arg Asn Asn Leu Val Asp Leu Tyr Asn Asn Ala Ser Ser Leu 594
     567                                                                 GAG
ATA ACT AAA ACA CTA GAT CCA CTA AAT GGG GGA ATG CTT TTA GAT TCT AAT GAG
Ile Thr Lys Thr Leu Asp Pro Leu Asn Gly Gly Met Leu Leu Asp Ser Asn Glu 648
     621                                                                 CAA
ATT ACT ACA GTT AAT CGG AAT ATT AAT ACG TTA TCA ACT ATT AAT GAA CAA
Ile Thr Thr Val Asn Arg Asn Ile Asn Thr Leu Ser Thr Ile Asn Glu Gln Gln 702
     675                                                                 AAT
AAG ACT AAT GCT GAT GCA TTA TCT AAT AGT TTT ATT AAA AAA GTG ATT CAA AAT
Lys Thr Asn Ala Asp Ala Leu Ser Asn Ser Phe Ile Lys Lys Val Ile Gln Asn 756
     729                                                                 AAC
AAT GAA CAA AGT TTT GTA GGG ACT TTT ACA AAC GCT AAT GTT CAA CCT TCA AAC
Asn Glu Gln Ser Phe Val Gly Thr Phe Thr Asn Ala Asn Val Gln Pro Ser Asn 810
     783                                                                 GCA
TAC AGT TTT GTT GCT TTT AGT GCT GAT GTA ACA CCC GTC AAT TAT AAA TAT GCA
Tyr Ser Phe Val Ala Phe Ser Ala Asp Val Thr Pro Val Asn Tyr Lys Tyr Ala

837
AGA AGA ACG GTT TGA AAT GGT GAT GAA CCT TCA AGT AGA ATT C
Arg Arg Thr Val .
```

Figure 4:
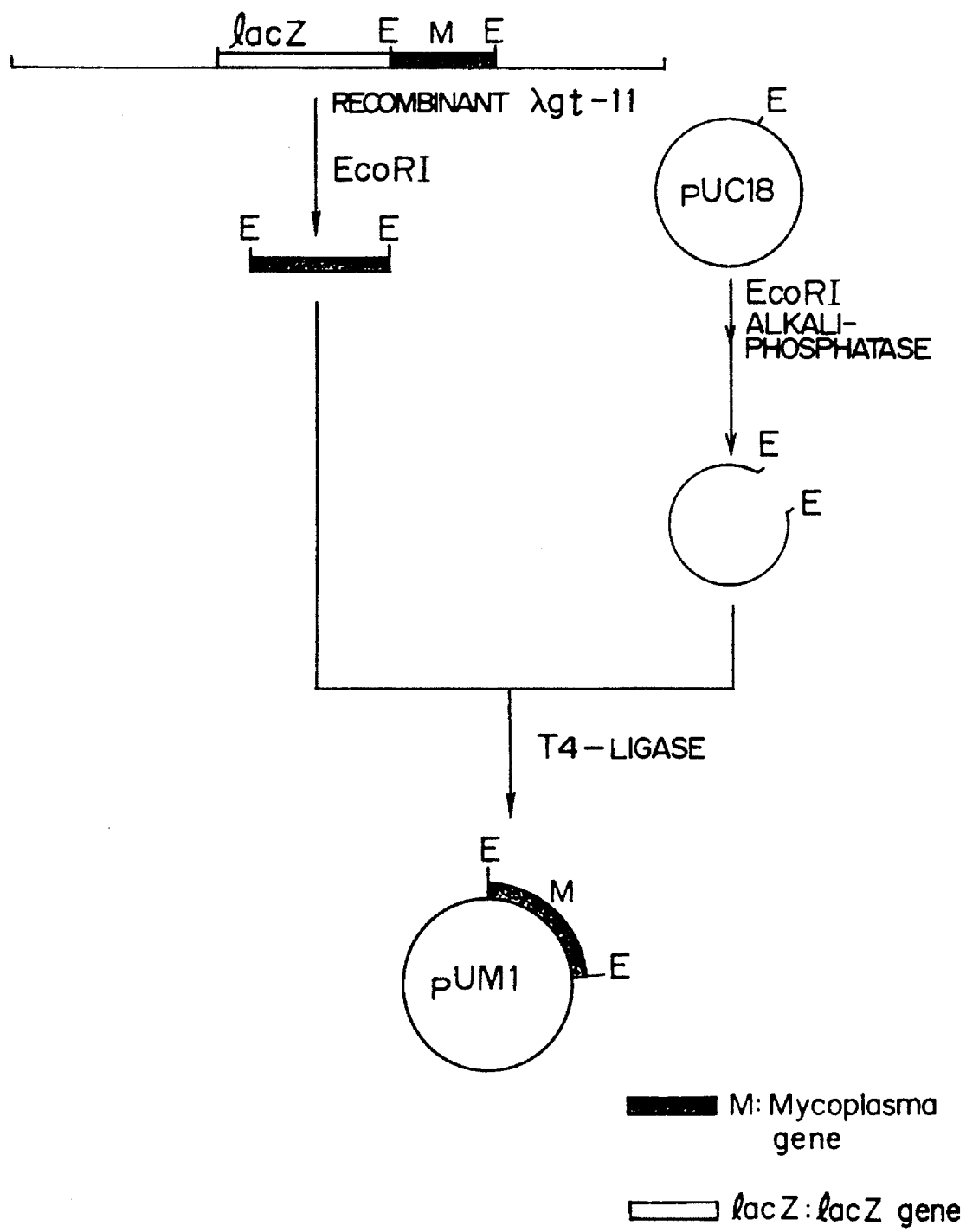

FIG. 3-4
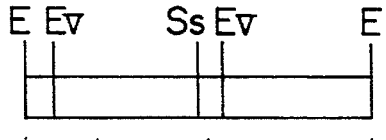
(s) M-19
0  0.2  0.5  0.95(Kbp)
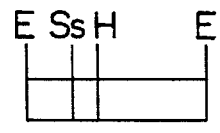
(t) M-20
0  0.2  0.5(Kbp)
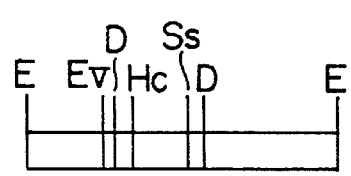
(u) M-21
0  0.2  0.5  0.85(Kbp)
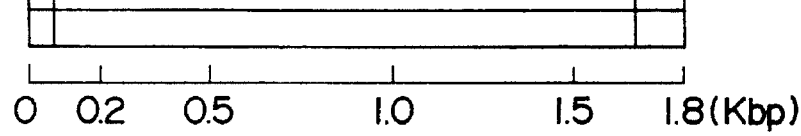
(v) M-22
0  0.2  0.5  1.0  1.5  1.8(Kbp)
E : EcoRI      D : DraI      Hf : Hinf I     R : Rsa I
PvII : PvuII   HaII : HaeII  P : Pst I       Sa : Sac I
Sc : Sca I     H : HindIII   PvI : PvuI      HpI : HpaI
Hc : HincII    Xb : XbaI     Ev : EcoRV      Sm : SmaI
Ba : BalI      Ss : SspI

POULTRY MYCOPLASMA ANTIGENS AND RECOMBINANT VECTORS CONTAINING THE GENE AS WELL AS DIAGNOSTICS AND VACCINES UTILIZING THE SAME

This application is a continuation of application Ser. No. 07/888,320, filed May 27, 1992, now abandoned, which is a continuation of 07/359,779, filed May 31, 1989, now abandoned.

BACKGROUND OF THE INVENTION

1. Field of the Invention

The present invention relates to antigen proteins of *Mycoplasma gallisepticum* that are infections to poultry, genes encoding the antigen proteins, recombinant vectors integrated with the genes encoding the antigen proteins, hosts transformed by the vectors, as well as poultry diagnostics and vaccines for *Mycoplasma gallisepticum* infections utilizing the antigen proteins produced by the hosts.

2. Discussion of Prior Art

*Mycoplasma gallisepticum* infectious disease that is one of the most serious infections on poultry such as chickens, is characterized by chronic respiratory disturbance accompanied by inflammation of the air sac in a chicken. A chicken infected with *Mycoplasma gallisepticum* as a pathogen develops very slight symptoms and rarely comes to death. However, when infected with *Mycoplasma gallisepticum*, an egg-laying rate and a hatching rate of eggs produced by infected chickens are markedly reduced. As a result, shipping of eggs and egg-laying chickens are decreased, resulting in considerable economic loss. In addition, *Mycoplasma gallisepticum* infection induces the reduction in immunity so that chickens are liable to suffer from other infectious diseases and to cause complication of severe infectious diseases. Furthermore, *Mycoplasma gallisepticum* is known to be a pathogen of infectious paranasal sinusitis in turkeys.

Efforts have been hitherto made to prevent poultry *Mycoplasma gallisepticum* infections using antibiotics or by vaccination and to establish pathogen-free poultry. However, administration of antibiotics involves defects that bacilli resistant to Mycoplasma would appear and Mycoplasma would readily proliferate after discontinuation of administration of antibiotics. On the other hand, prophylaxis by vaccination using attenuated Mycoplasma might cause opportunistic infections with other pathogens, or *Mycoplasma gallisepticum* infections. As stated above, it is highly difficult to establish and maintain a group of poultry free of infections with Mycoplasma.

Turning to a determination of whether or not poultry is infected with *Mycoplasma gallisepticum*, it has been judged by determining if serum collected from poultry could inhibit proliferation of Mycoplasma to form a characteristic inhibition zone on PPLO agar plate including glucose and donor horse serum. However, the method involves shortcomings that 3 to 7 days are required to judge whether or not a clear inhibition zone is formed; during the period, infection tends to be spread over the whole group of poultry.

As a result of extensive investigations to solve the drawbacks in the prior art, the present inventors have discovered polypeptides derived from *Mycoplasma gallisepticum* and having antigenicity of *Mycoplasma gallisepticum* and further found that antisera, derived from the polypeptides using said polypeptides as antigens, can prevent growth of *Mycoplasma gallisepticum* and, the polypeptides are expected to be useful as poultry vaccines capable of preventing *Mycoplasma gallisepticum* infections and are useful as poultry diagnostics for *Mycoplasma gallisepticum* infections. The present invention has thus come to be accomplished.

SUMMARY OF THE INVENTION

According to a first aspect of the present invention, there is provided polypeptides which causes an antigen-antibody reaction with anti-*Mycoplasma gallisepticum* poultry sera.

According to a second aspect of the present invention, there is provided a gene encoding the polypeptides.

According to a third aspect of the present invention, there is provided a recombinant vector in which the gene has been integrated.

According to a forth aspect of the present invention, there is provided a host transformed or transfected by the recombinant vector.

According to a fifth aspect of the present invention, there is provided a poultry vaccine for *Mycoplasma gallisepticum* infections comprising the polypeptides as an effective ingredient.

Further according to a sixth aspect of the present invention, there is provided a poultry diagnostic for *Mycoplasma gallisepticum* infection comprising the polypeptides as an effective ingredient.

BRIEF DESCRIPTION OF THE DRAWINGS

FIG. 1(*a*)-1 to 1(*f*)-2 shows amino acid sequences of polypeptides MG-1, MG-2, MG-3, MG-7, MG-8 and MG-9 exhibiting antigenicity of *Mycoplasma gallisepticum* and base sequences of M-1, M-2, M-3, M-7, M-8 and M-9 encoding the polypeptides. FIG. 2(*a*) and 2(*b*) similarly shows an amino acid sequence of polypeptide TMG-1 and a base sequence of TM-1 encoding the polypeptide. FIG. 3-1 to 3-4 indicate restriction enzyme cleavage maps of DNA fragments encoding the polypeptides in accordance with the present invention. FIGS. 4, 5 and 6 indicate procedures for producing antigen protein plasmids in accordance with the present invention.

DETAILED DESCRIPTION OF PREFERRED EMBODIMENTS

In the first aspect of the present invention, the polypeptides are the one that cause an antigen-antibody reaction with poultry sera infected with *Mycoplasma gallisepticum*.

Specific examples include DNA fragments derived from *Mycoplasma gallisepticum* and polypeptides that can be produced by fragments having restriction enzyme cleavage maps shown in FIG. 3, (a) through (v). More specifically, the polypeptides are as shown in Table 1 and exemplified by about 30 kilodaltons of polypeptide MG-1 derived from cloned antigen DNA M-1, about 1 kilodalton of polypeptide MG-2 derived from cloned antigen DNA M-2, about 30 kilodaltons of polypeptide MG-3 derived from cloned antigen DNA M-3, about 55 kilodaltons of polypeptide MG-4 derived from cloned antigen DNA M-4, about 1 kilodalton of polypeptide MG-5 derived from cloned antigen DNA M-5, about 32 kilodaltons of polypeptide MG-6 derived from cloned antigen DNA M-6, about 35 kilodaltons of polypeptide MG-7 derived from cloned antigen DNA M-7, about 35 kilodaltons of polypeptide MG-8 derived from cloned antigen DNA M-8, about 35 kilodaltons of polypeptide MG-9 derived from cloned antigen DNA M-9, about 55 kilodaltons of polypeptide MG-10 derived from cloned antigen DNA M-10, about 46 kilodaltons of polypeptide MG-11 derived from cloned antigen DNA M-11, about 15 kilodaltons of polypeptide MG-12 derived from cloned antigen DNA M-12, about 29 kilodaltons of polypeptide MG-13 derived from cloned antigen DNA M-13, about 15 kilodaltons of polypeptide MG-14 derived from cloned antigen DNA M-14, about 79 kilodaltons of polypeptide MG-15 derived from cloned antigen DNA M-15, about 15 kilodaltons of polypeptide MG-16 derived from cloned antigen DNA M-16, about 55 kilodaltons of polypeptide MG-17 derived from cloned antigen DNA M-17, about 49 kilodaltons of polypeptide MG-18 derived from cloned antigen DNA M-18, about 32 kilodaltons of polypeptide MG-19 derived from cloned antigen DNA M-19, about 35 kilodaltons of polypeptide MG-20 derived from cloned antigen DNA M-20, about 9 kilodaltons of polypeptide MG-21 derived from cloned antigen DNA M-21, about 38 kilodaltons of polypeptide MG-22 derived from cloned antigen DNA M-22, etc. The polypeptide is further exemplified by a polypeptide having amino acid sequence containing the amino acid sequence from one of these polypeptides and having the same amino acid sequence as the polypeptide expressed in *Mycoplasma gallisepticum*. The polypeptide is also exemplified by fused proteins having as C-terminus an amino acid sequence of MG-1, MG-2, MG-3, MG-7, MG-8, MG-9 shown in FIG. 1 (a)-1 through (f)-2 or TMG-1 shown in FIG. 2(a) and 2(b) and containing, as stabilizing protein, bacteria-derived enzyme proteins such as β-galactosidase, β-lactamase, etc. at the N-terminus thereof. Other polypeptides can also be converted into fused proteins with bacteria-derived enzyme proteins.

The polypeptides which are concerned with the first aspect of the present invention can be obtained by using the host (relating to the forth aspect of the invention) transformed or transfected by the recombinant vector that is concerned with the third aspect of the invention.

The recombinant vector described above can be obtained by integrating a *Mycoplasma gallisepticum*-derived DNA fragment into an expression vector in a conventional manner.

Sources for collecting the DNA fragment may be any one so long as they belong to *Mycoplasma gallisepticum*. Specific examples include S6 strain (ATCC 15302), PG31 (ATCC 19610) and the like.

Figures 2, 3:
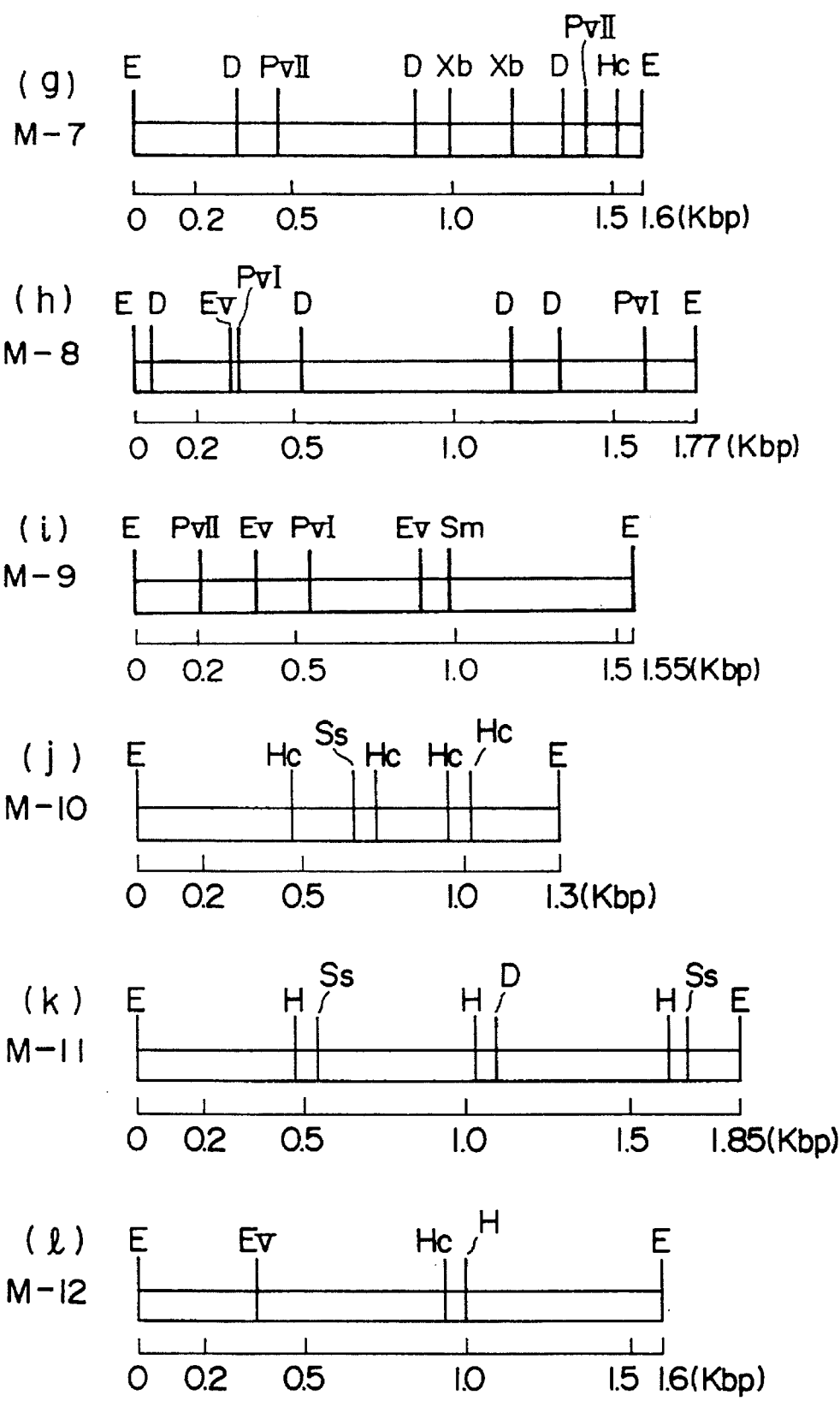
Figure 3:
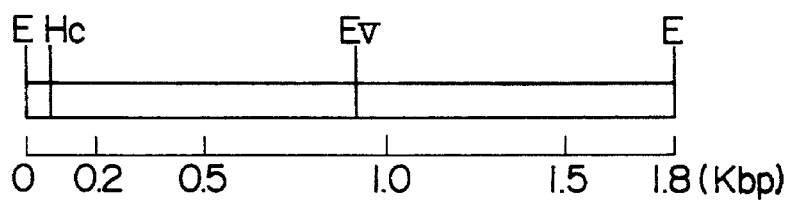
Figure 3:
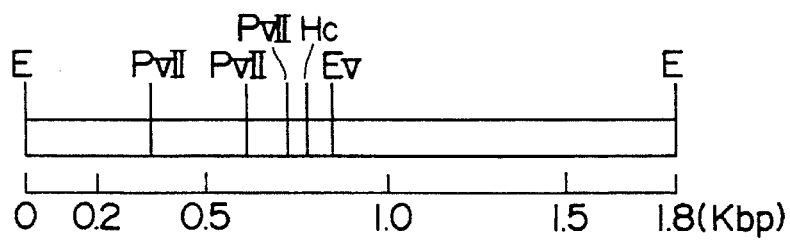
Figure 3:
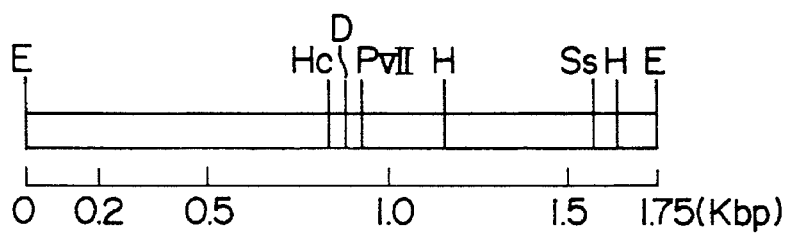
Figure 3:
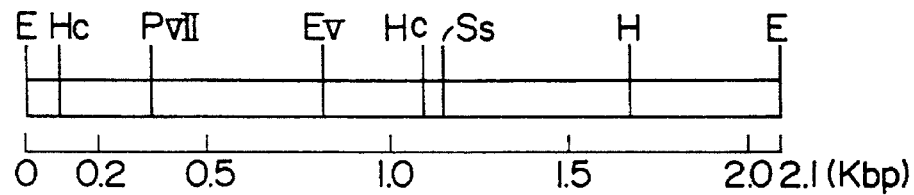
Figure 3:
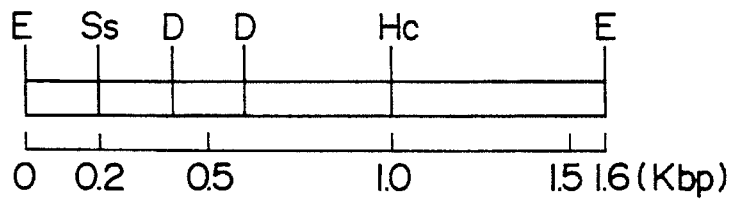
Figure 3:
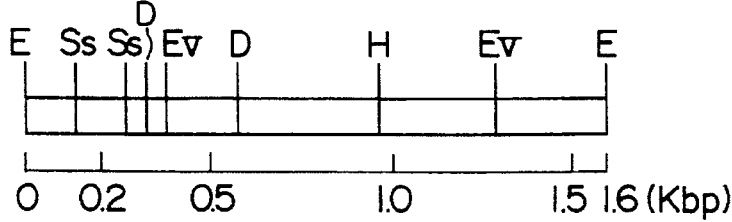

Specific examples of the DNA fragment used for recombination are DNA fragment encoding the amino acid sequence shown in FIG. 1(a)-1 and FIG. 1(a)-2 (for example, 705 base pairs from 1 to 705 in FIG. 1(a)-1 and FIG. 1(a)-2), DNA fragment encoding the amino acid sequence shown in FIG. 1(b) (for example, 30 base pairs from 1 to 30 in FIG. 1(b)), DNA fragment encoding the amino acid sequence shown in FIG. 1(c) (for example, 657 base pairs from 1 to 657 in FIG. 1(c)), DNA fragment encoding the amino acid sequence shown in FIG. 1(d) (for example, 549 base pairs from 1 to 549 in FIG. 1(d)), DNA fragment encoding the amino acid sequence shown in FIG. 1(e) (for example, 927 base pairs from 1 to 927 in FIG. 1(e)), DNA fragment encoding the amino acid sequence shown in FIG. 1(f)-1 and FIG. 1(f)-2 (for example, 531 base pairs from 1 to 531 in FIG. 1(f)-1 and FIG. 1(f)-2); and DNA fragments added at the upstream of the 5' end thereof with a DNA fragment encoding enzyme protein, etc. of bacteria in combination with the reading frame. In addition thereto, the DNA fragment is also exemplified by DNA fragments derived from *Mycoplasma gallisepticum* such as M-4, M-5, M-6, M-10, M-11, M-12, M-13, M-14, M-15, M-16, M-17, M-18, M-19, M-20, M-21, M-22, etc. Restriction enzyme cleavage maps of these DNA fragments and their lengths are shown in FIG. 3. Furthermore, the DNA fragment is exemplified by the one, encoding the amino acid sequence of that having the same amino acid sequence as that of the polypeptide expressed in *Mycoplasma gallisepticum* and containing the amino acid sequence of these antigen polypeptide, etc. (for example, 783 base pairs from 40 to 822 in FIG. 2), given from genomic DNA of *Mycoplasma gallisepticum* in such a manner well known to one skilled in the art as the hybridization technique using these DNA fragments as probes.

The vector which is used to construct the recombinant vector is not particularly limited, however, specific examples include plasmids such as pUC8, pUC9, pUC10, pUC11, pUC18, pUC19, pBR322, pBR325, pBR327, pDR540, pDR720, and the like; phages such as λgt11, λgt10, λEMBL3, λEMBL4, Charon 4A and the like.

The method for inserting the DNA fragment described above into these vectors to produce recombinant vectors may be performed in a manner conventional to one skilled in the art. For example, the vector is cleaved with a restriction enzyme and ligated with the DNA fragments described above either directly or via synthetic linker, under control of a suitable expression regulatory sequence.

As the expression regulatory sequence used, those may be mentioned; lac promoter operator, trp promoter, tac promoter, lpp promoter, $P_L$ promoter, amyE promoter, Gal7 promoter, PGK promoter, ADH promoter, etc.

In producing the recombinant vector for the purpose of expressing these polypeptides derived from Mycoplasma, techniques for producing a recombinant vector by once integrating the aforesaid DNA fragment into a suitable vector and then carrying out subcloning, is well known to one skilled in the art. These subcloned DNA fragments are excised with an appropriate restriction enzyme and ligated under control of the expression regulatory sequence described above. Thus, the recombinant vector capable of producing the polypeptide can be produced.

The vector which is used for the subcloning is not critical but specific examples include plasmids such as pUC8, pUC9, pUC10, pUC11, pUC18, pUC19, pBR322, pBR325, pBR327, pDR540, pDR720, pUB110, pIJ702, YEp13, YEp24, YCp19, YCp50, and the like.

Using the obtained recombinant vector, a variety of appropriate hosts are transformed to microorganisms that can produce the polypeptides capable of expressing antigenicity of *Mycoplasma gallisepticum*, a part of the polypeptides or a fused protein containing said polypeptides.

The appropriate host used herein can be chosen taking into account adaptability to expression vector, stability of the products, etc. Specific examples are genus Escherichia (for example, *Escherichia coli*), genus Bacillus (for example, *Bacillus subtilis, Bacillus sphaericus*, etc.), Actinomyces, Saccharomyces, etc. The host transformed with an appropriate expression vector can be cultured and proliferated under suitable culture conditions well known to one skilled in the art.

Upon production of the polypeptide, conditions for inducing the action of expression regulation sequence can be chosen. More specifically, in the case of lac promoter operator, such conditions can be effected by adding a suitable quantity of isopropylthio-β-D-galactopyranoside to a culture solution.

The poultry vaccine for *Mycoplasma gallisepticum* infections can be prepared in a manner similar to conventional technique from the thus obtained host which is concerned with the forth aspect of the invention. The host can be cultured under conditions ordinarily used for culturing microorganisms of this type. In the case of *E. coli,* the bacteria can be cultured in LB medium at 37° C. under aerobic conditions.

After culturing, the polypeptide of the present invention can be purified by means of chromatography, precipitation by salting out, density gradient centrifugation and the like which are well known to one skilled in the art and may optionally be chosen. The thus obtained polypeptide can be used as a vaccine.

Alternatively, the host can be inactivated and the inactivated host can be used as a vaccine. In this case, the inactivation is carried out in a conventional manner after culture of the host is completed. The inactivation may be attained by heating but it is simpler to add an inactivating agent to the culture solution. As the inactivating agent, there may be used Merzonin (trademark, thimerosal manufactured by Takeda Pharmaceutical Co., Ltd.; hereinafter the same), β-propiolactone, tyrosine, salicylic acid, Crystal Violet, benzoic acid, benzetonium chloride, polymyxin, gramicidin, formalin, phenol, etc. The inactivated culture solution is added, if necessary and desired, with a suitable quantity of adjuvant. The inactivated product is then separated with a siphon or by means of centrifugation, etc. As the adjuvant, aluminum hydroxide gel, aluminum phosphate gel, calcium phosphate gel, alum, etc. are employed. The inactivated product thus separated is adjusted with phosphate buffered saline, etc. to a suitable concentration. If necessary and desired, an antiseptic is added to the product. Examples of the antiseptic which can be used include Merzonin, β-propiolactone, tyrosine, salicylic acid, Crystal Violet, benzoic acid, benzetonium chloride, polymyxin, gramicidin, formalin, phenol, etc.

In order to further enhance immune activity, adjuvant may also be added to the obtained vaccine. The adjuvant is generally used in a volume of 1 to 99 based on 100 volume of the vaccine.

When the vaccine is used, it can be mixed with diluents, filler, etc. in a conventional manner. The vaccine exhibits the effect with a dose of at least 1 µg antigenic polypeptide per kg wt. The upper limit is not critical unless the does shows acute toxicity. The dose can be determined opportunely, for example, under such conditions that the counteractive antibody titer ($\log_{10}$) is 1.0 to 2.0. No acute toxicity was notable with a dose of 5 mg antigenic polypeptide per kg wt. to chickens.

The poultry vaccine for *Mycoplasma gallisepticum* infection obtained in the present invention is inoculated to poultry intramuscularly, subcutaneously or intracutaneously, etc.

Likewise the vaccine, the polypeptide of the present invention obtained by purification and isolation can be used as diagnostics since the polypeptide can strongly bind to antibody in sera collected from poultry infected with *Mycoplasma gallisepticum*. A test sample can be diagnosed with respect to *Mycoplasma gallisepticum* infections, by methods well known to one skilled in the art, such as by ELISA which comprises immobilizing the polypeptide onto a microtiter plate, reacting with poultry serum which is a test sample, then reacting with a secondary antibody labeled with peroxidase, etc. and peroxidase substrate and, determining a change in absorbancy of the reaction solution; etc.

According to the present invention, the polypeptides having antigenicity derived from *Mycoplasma gallisepticum* can be provided. The recombinant vectors in which DNAs encoding these polypeptides can also be provided. Furthermore, microorganisms such as bacteria, yeast, etc. transformed (or transfected) by these recombinant vectors can be provided. The polypeptides produced by these microorganisms have the same antigenicity as that of the polypeptide derived from *Mycoplasma gallisepticum*. Using the polypeptides, more effective vaccines and poultry diagnostics for *Mycoplasma gallisepticum* infection which are handled in more rapid and simpler way can be provided.

Hereafter the present invention is described in more detail by referring to the examples below. In the examples and comparative examples as well as reference examples, parts and % are all by weight, unless otherwise indicated.

EXAMPLE 1

(1) Preparation of genomic DNA of *Mycoplasma gallisepticum*

*Mycoplasma gallisepticum* S6 strain was cultured at 37° C. for 3 to 5 days in liquid medium obtained by supplementing 20% donor horse serum, 5% yeast extract, 1% glucose and a trace amount of phenol red as a pH indicator in 100 ml of PPLO broth basal medium. As *Mycoplasma gallisepticum* proliferated, pH of the culture solution decreased. At the point of time when the color of the pH indicator contained in the culture solution changed from red to yellow, incubation was terminated. The culture solution was centrifuged at 10,000 rpm for 20 minutes to collect the cells. The collected cells were then suspended in 1/10 volume of PBS based on the volume of culture solution. The suspension was again centrifuged at 10,000 rpm for 20 minutes to collect the cells. The collected cells were resuspended in 2.7 ml of PBS and SDS was added thereto in a concentration of 1%. Furthermore 10 µg of RNase was added to the mixture. The mixture was incubated at 37° C. for 30 minutes to cause lysis.

The lysate was extracted 3 times with an equal volume of phenol and then 3 times with ethyl ether. The extract was precipitated with ethanol to give 200 µg of genomic DNA of *Mycoplasma gallisepticum*.

(2) Construction of genomic DNA library

To 40 µg of the genomic DNA of *Mycoplasma gallisepticum* obtained in (1) was added 4 units of restriction enzyme Alu I. The mixture was incubated at 37° C. for 10 minutes to cause partial cleavage. The partially cleaved genomic DNA was subjected to 0.8% low melting point agarose gel electrophoresis. A DNA fragment having a length of from about 1.0 kbp to about 4.0 kbp was recovered from the gel, treated with phenol and precipitated with ethanol to give 4 µg of the DNA fragment partially cleaved with Alu I.

S-Adenosyl-L-methionine was added to 1.2 µg of the DNA fragment partially cleaved with Alu I in a final concentration of 80 µM, and 20 units of EcoR I methylase was further added thereto to methylate the deoxyadenosine site in EcoR I recognition sequence, whereby the sequence was rendered insensitive to EcoR I. EcoR I linker was ligated with the DNA fragment by ligase and further mixed with a fragment of λgt11 DNA cleaved with EcoR I. Ligation was performed by ligase. Using the reaction solution, in vitro packaging was carried out in a conventional manner (DNA Cloning, vol. 1, A Practical Approach, edited by D. M. Glover). The packaging product was transfected to *E. coli* Y1088 (Amersham Inc.), which was then cultured at 37° C. for 12 hours in LB agar medium containing 0.003% of 5-bromo-4-chloro-3-indolyl-β-D-galactopyranoside and 0.03 mM of isopropylthio-β-D-galactopyranoside (IPTG). In the formed plaques, a library size was estimated by the number of white plaques and $10^6$ pfu (plaque forming unit) of DNA library was prepared.

(3) Immunoscreening of genomic DNA library

Phage obtained from the DNA library prepared in (2) was added to a suspension of *E. coli* Y1090 (Amersham Inc.) in 10 mM MgSO₄ aqueous solution in such a way that 500 to 1000 plaques were formed in a plate of 8 cmø, which was allowed to adsorb for 15 minutes. Furthermore, 2.5 ml of LB soft agar medium heated to 45° C. was added and overlaid on the LB agar medium to form layers. Incubation was conducted at 42° C. for 3 to 4 hours. A nylon membrane filter was immersed in 10 mM IPTG aqueous solution. After air drying, the filter was overlaid on the plate described above followed by incubation at 37° C. for further 2 to 3 hours. After the incubation, the nylon membrane filter was stripped off from the plate and washed with TBS (50 mM Tris-HCl, pH 8.0, 150 mM NaCl). After further immersing in TBS containing 2% of skimmed milk for 30 minutes, the filter was immersed for an hour with anti-Mycoplasma chicken serum diluted with TBS to 500-fold. Thereafter, the filter was washed by immersing in TBS for 15 minutes. The filter was further washed by immersing in TBS containing 0.05% of surfactant (Tween 20) for 10 to 15 minutes. The washing procedure was repeated 4 or 5 times. Then, the filter was treated for 60 minutes with biotinated antibody to chicken IgG. After treating with a secondary antibody, the filter was washed 5 or 6 times with PBS containing 0.05% of Tween 20 and further immersed in horse radish peroxidase-avidin D solution to treat the same for 60 minutes. After the treatment, the filter was washed 5 or 6 times with PBS containing 0.05% of Tween 20 and further washed with 10 mM Tris-HCl showing pH of 8.0. Thereafter the filter was immersed in buffer containing 4-chloronaphthol and hydrogen peroxide. By this series of procedures, only the plaque in which the antigen protein derived from *Mycoplasma gallisepticum* had been expressed was colored to purple.

By the immunoscreening of 5×10⁴ plaques described above, 50 positive plaques were obtained.

(4) Preparation of immunopositive recombinant λgt11 phage DNA

*E. coli* Y 1090 strain was cultured at 37° C. for 12 hours in LB medium containing 50 µg/ml of ampicillin and the culture solution was added to 10-fold volume of LB medium containing 10 mM $MgSO_4$. Then, recombinant λgt11 phage obtained in (3) which had been determined to be positive in the immunoscreening was infected to *E. coli* Y1090 at moi of 0.05 followed by culturing at 37° C. for 5 to 10 hours. After *E. coli* was lysed, centrifugation was performed at 8,000 rpm for 10 minutes to obtain the supernatant. An equal volume of TM buffer (50 mM Tris-HCl, pH 7.4, 10 mM $MgSO_4$) as well as DNase I were so added to the supernatant to show the concentration of 0.016 mg/ml followed by incubation for 15 minutes. Furthermore, NaCl and polyethylene glycol (PEG 6000) were so added thereto as to show the concentration of 0.5 M and 0.1 g/ml. The mixture was shaken at 0° C. for 15 minutes. The resulting mixture was centrifuged at 10,000 rpm for 10 minutes to remove the supernatant. The obtained pellets were dissolved in 1/100 volume of TM buffer and an equal volume of chloroform was added to the mixture followed by vigorous stirring. The mixture was centrifuged at 15,000 rpm for 10 minutes and recombinant λgt11 phage was collected in the aqueous phase to obtain a phage solution.

To the phage solution were so added EDTA, SDS and pronase E as to show the concentration of 0.025M, 1%, 1 mg/ml. After incubation at 37° C. for 4 hours, the solution was extracted with phenol (3 to 5 times). The extract was precipitated with ethanol to give λgt11 phage DNA containing cloned antigen DNA (M-1).

(5) Removal of the same clone from immunopositive recombinant λgt11 phage

After digesting 1 μg of each λgt11 phage. DNA obtained in (4) with EcoR I, *Mycoplasma gallisepticum*-derived DNA was recovered by means of 0.8% low melting point agarose gel electrophoresis. The DNA was used as probe DNA.

*E. coli* Y1090 strain was cultured in LB medium at 37° C. for 12 hours. 100 μl of the culture was mixed with 3 ml of LB soft agar medium warmed at 45° C. and the mixture was overlaid on LB agar medium. On the medium 10 μl each of the respective λgt11 clones was dropped onto definite positions. When cultured at 37° C. for 12 hours, plaques due to phage proliferation were formed at the dropped positions. A nylon membrane was put on this plate and the phage was adsorbed thereto. After air drying, the membrane was treated with a denaturing solution (0.5 M NaOH, 1.5 M NaCl) for 10 minutes and further treated with a neutralizing solution (3 M sodium acetate, pH 5.5) for 10 minutes. After air drying, the membrane was heated at 80° C. for 2 hours. 4-Fold SET (0.6 M NaCl, 0.08 M Tris-HCl, 4 mM EDTA, pH 7.8),10-fold Denhardt, 0.1% SDS, 0.1% $Na_4P_2O_7$,50 μg/ml of denatured salmon sperm DNA and the *Mycoplasma gallisepticum*-derived DNA probe which had been previously prepared and labeled in a conventional manner were added to cause hybridization at 68° C. for 14 hours. After washing, the nylon membrane was overlaid on an X ray film. The presence of spot was confirmed by autoradiography. A plaque in which a spot was formed was removed as the same plaque. It was thus confirmed that 22 clones were independent.

(6) Production of recombinant plasmid (pUM1) (cf. FIG. 4)

After digesting the recombinant λgt11 phage DNA obtained in (5) with restriction enzyme EcoR I, the digestion product was subjected to 0.8% low melting point agarose gel electrophoresis. Genomic DNA fragment of *Mycoplasma gallisepticum* integrated into cloning site of the genomic DNA of λgt11 phage showed a length of about 0.8 kbp. The DNA fragment was extracted from the agarose gel and further extracted with phenol-chloroform (1:1). The extract was precipitated with ethanol and the precipitates were recovered. On the other hand, plasmid pUC18 was similarly digested with EcoR I. Then, the digestion product was extracted with phenol-chloroform. The extract was precipitated with ethanol and cleaved pUC18 was recovered. Then 5' end phosphate was removed by treating with alkaline phosphatase. After pUC18 DNA was again extracted with phenol-chloroform, DNA was recovered by ethanol precipitation.

The cleaved pUC18 was ligated with the *Mycoplasma gallisepticum* genome-derived EcoR I digestion product (about 0.8 kbp) by ligase and competent *E. coli* TG1 strain was transformed. The transformants were cultured at 37° C. for 15 hours in LB agar medium containing 0.003% of 5-bromo-4-chloro-3-indolyl-β-D-galactopyranoside, 0.03 mM of isopropylthio-β-D-galactopyranoside and 40 μg/ml of ampicillin. Among transformed *E. coli* grown on the agar medium, white colonies were cultured at 37° C. for 15 hours in LB liquid medium containing 40 μg/ml of ampicillin and plasmids were extracted by the method of Birnboim & Doly [Nucleic Acid Research, 7, 1513 (1979)]. After digesting with EcoR I, recombinant plasmid containing a DNA fragment having the same length of the original EcoR I fragment derived from *Mycoplasma gallisepticum* was detected by 0.8% low melting point agarose gel electrophoresis and named pUM1. The plasmid pUM1 is the recombinant vector of the present invention.

(7) Sequence analysis of pUM1 insert DNA Sequence of insert DNA fragment was determined by the Dideoxy method of Sanger et al. [Proc. Natl. Acad. Sci., USA, 74, 5463 (1977)] using pUM1 prepared in (6). A restriction enzyme cleavage map of the cloned DNA fragment is shown in FIG. 3 (a) and the nucleotide sequences of the DNA fragment are shown in FIG. 1(a)-1 and FIG. 1(a)-2.

From the facts that a molecular weight of the fused protein with β-galactosidase produced in (9) later described was about 145 kilodaltons and translation termination codon (TGA) was present in bases of 706 to 708 in FIG. 1(a)-2, it is noted that the fragment encoding the polypeptide exhibiting antigenicity of *Mycoplasma gallisepticum* is 705 bp from 1 to 705 in FIG. 1(a)-1 and FIG. 1(a)-2 and the amino acid sequence deduced from the sequence is as shown in FIG. 1(a)-1 and FIG. 1(a)-2.

Figure 5:
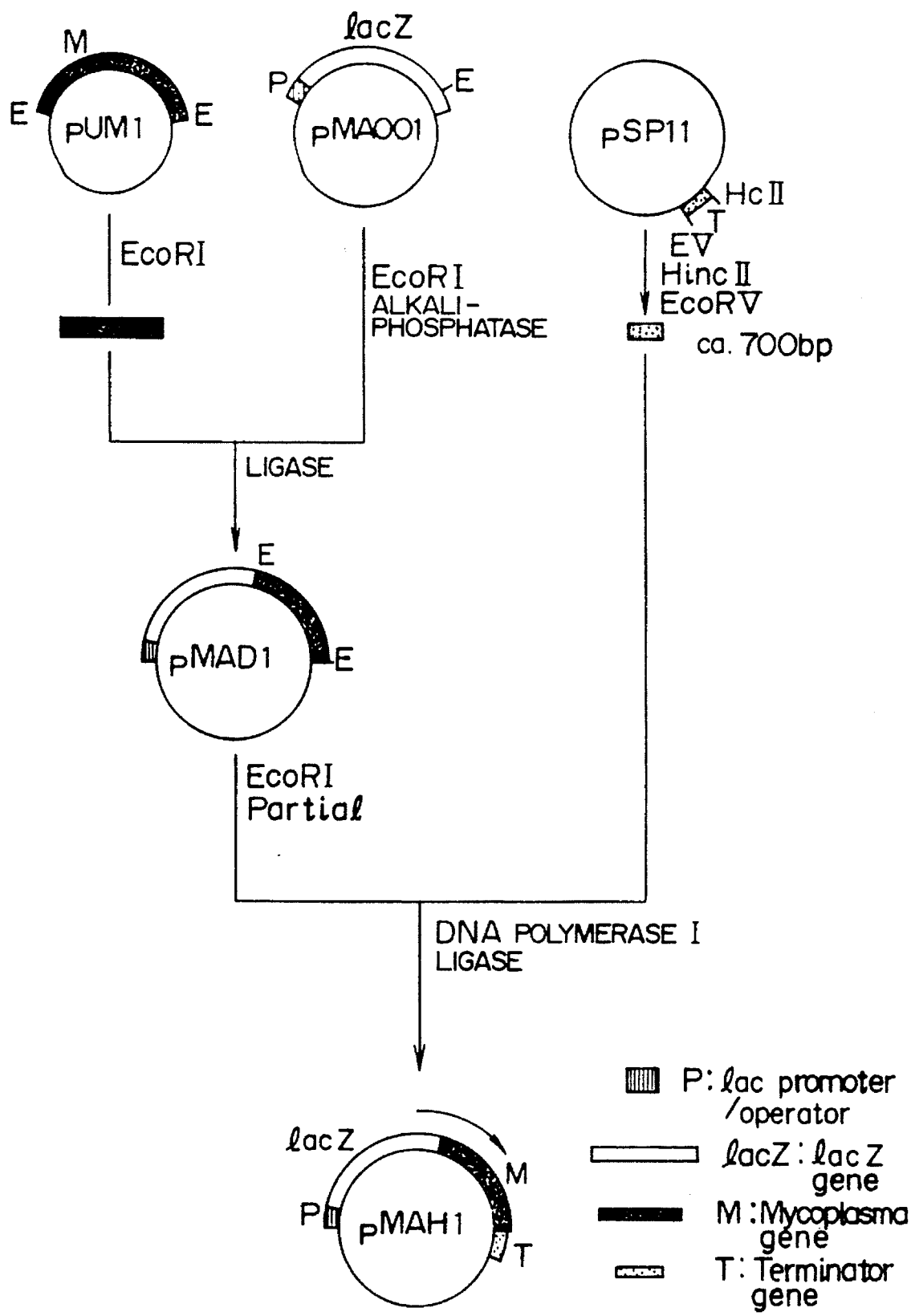

(8) Production of plasmid capable of expressing antigen protein (cf. FIG. 5)

The recombinant plasmid (pUM1) obtained in (6) was digested with EcoR I. The digestion product was subjected to 0.8% low melting point agarose gel electrophoresis. Insert DNA having a length of about 0.8 kbp was recovered from the gel and extracted with phenol-chloroform. The extract was precipitated with ethanol to recover DNA.

On the other hand, plasmid pMA001 [Gene, 28, 127–132 (1984)] harboring lac promoter-operator and lac Z gene was digested with EcoR I. After the digestion product was extracted with phenol-chloroform, the extract was precipitated with ethanol and cleaved pMA001 was recovered. Then, 5' end phosphate was removed by treating with alkaline phosphatase. After again extracting with phenol-chloroform, pMA001 DNA was recovered by ethanol precipitation.

The cleaved pMA001 was ligated with the EcoR I digestion product (about 0.8 kbp) of insert DNA by ligase and competent *E. coli* TG1 strain was transformed. A recombinant plasmid capable of expressing as a fused protein with β-galactosidase in which about 0.8 kbp of genomic DNA of *Mycoplasma gallisepticum* had been ligated in the correct direction at the downstream of lac Z gene of pMA001 was selected in a manner similar to (6). The recombinant plasmid was named pMAD1. This plasmid is the recombinant vector of the present invention.

Then, pMAD1 was partially digested with EcoR I. The partial digestion product was subjected to 0.8% low melting point agarose gel electrophoresis. About 7.2 kbp of fragment obtained by cleaving pMAD1 with EcoR I at one site was recovered from the agarose gel. After treating with phenol-chloroform, cleaved pMAD1 was recovered by ethanol precipitation.

On the other hand, pSP11 [Journal of Bacteriology, June 1986, 937–944] was doubly cleaved with Hinc II and EcoR V. The cleavage product was subjected to 1.0% low melting point agarose gel electrophoresis. About 700 bp of fragment containing transcription termination sequence was recovered. After similarly treating with phenol-chloroform, the DNA fragment was recovered by ethanol precipitation. The cleaved pMAD1 and about 700 bp of DNA fragment containing transcription termination sequence were combined and cohesive ends of the respective DNA fragments were rendered blunt ends by DNA-polymerase I (Klenow's fragment). They were further ligated with ligase and competent *E. coli* TG1 strain was transformed. A recombinant plasmid in which the transcription termination sequence had been inserted at the downstream of genomic DNA of *Mycoplasma gallisepticum* of pMAD1 was selected in a manner similar to (6). The recombinant plasmid was named pMAH1. This plasmid is the recombinant vector of the present invention.

(9) Expression and detection of antigen protein (β-galactosidase fused protein)

(9-a) *E. coli* (MC169 strain) transformed with the recombinant plasmid obtained in (8) was precultured at 37° C. overnight in LB medium containing 50 μg/ml of ampicillin. 1 ml of the preculture was taken and added to 100 ml of LB liquid medium likewise containing 50 μg/ml of ampicillin followed by culturing at 37° C. Two hours later, isopropylthio-β-D-galactopyranoside was so added thereto as to show the concentration of 1 mM followed by culturing at 37° C. for further 5 hours. After the incubation, centrifugation was performed at 8,000 rpm for 10 minutes to collect *E. coli*. By adding 1.0 ml of PBS, *E. coli* was resuspended. The suspension was subjected to freezing and thawing. The cells were further sonicated and then centrifuged at 15,000 rpm for 30 minutes to recover the supernatant.

(9-b) Then, the supernatant was subjected to 8% SDS polyacrylamide gel electrophoresis (SDS-PAGE) at 50 mA for 2 hours. After the electrophoresis, the gel was stained with Coomassie Brilliant Blue R-250 to newly detect a band of about 145 daltons. pMA001-derived β-galactosidase (in part) is approximately 115 kilodaltons. It is thus considered that the newly formed polypeptide would correspond to fused protein MGg-1 in which about 30 kilodaltons of polypeptide MG-1 having *Mycoplasma gallisepticum*-derived amino acid sequence shown in FIG. 1(a) is jointed at the C-terminus of β-galactosidase.

(9-c) On the other hand, the supernatant described above was subjected to 8% SDS-PAGE in a manner similar to (9-b) and a protein band separated in the gel was then transferred onto a nylon membrane filter. After the transfer, the filter was reacted with anti-Mycoplasma serum by procedures as in (3) to perform Western blotting. As the result, only the band corresponding to the protein of about 145 kilodaltons newly found in (9-b) was detected. It was made clear that the protein was fused protein MGg-1 of *Mycoplasma gallisepticum*-derived antigen protein MG-1 and β-galactosidase.

EXAMPLE 2

A recombinant plasmid capable of expressing *Mycoplasma gallisepticum*-derived antigen protein was produced from immunopositive plaque to anti-sera of *Mycoplasma gallisepticum* obtained in Example 1 (3), by procedures similar to Example 1 (4), (5), (6) and (8). Cloning λ phage vector used and subcloning vector and expression vector used are shown in Table 1. Restriction enzyme cleavage maps and lengths of cloned *Mycoplasma gallisepticum* gene are shown in FIG. 3 (b) through (v).

Then, the expression vector described above was allowed to express in a manner similar to Example 1 (9), whereby a part of β-galactosidase and a fused protein were obtained. Molecular weights of fused proteins MGg-1 to MGg-22 and antigen proteins MG-1 to MG-22 derived from *Mycoplasma gallisepticum* are shown in Table 1, respectively.

TABLE 1

| Run No. | Cloning λ Vector | Subcloning Vector | Expression Vector | Fused Protein Name | kd | Mycoplasma-derived polypeptide Name | kd |
|---|---|---|---|---|---|---|---|
| 2-1 | M-1 | pUM1 | pMAH-1 | MGg-1 | 145 | MG-1 | 30 |
| 2-2 | M-2 | pUM2 | pMAH-2 | MGg-2 | 116 | MG-2 | 1 |
| 2-3 | M-3 | pUM3 | pMAH-3 | MGg-3 | 145 | MG-3 | 30 |
| 2-4 | M-4 | pUM4 | pMAH-4 | MGg-4 | 170 | MG-4 | 55 |
| 2-5 | M-5 | pUM5 | pMAH-5 | MGg-5 | 116 | MG-5 | 1 |
| 2-6 | M-6 | pUM6 | pMAH-6 | MGg-6 | 147 | MG-6 | 32 |
| 2-7 | M-7 | pUM7 | pMAH-7 | MGg-7 | 150 | MG-7 | 35 |
| 2-8 | M-8 | pUM8 | pMAH-8 | MGg-8 | 150 | MG-8 | 35 |
| 2-9 | M-9 | pUM9 | pMAH-9 | MGg-9 | 150 | MG-9 | 35 |
| 2-10 | M-10 | pUM10 | pMAH-10 | MGg-10 | 170 | MG-10 | 55 |
| 2-11 | M-11 | pUM11 | pMAH-11 | MGg-11 | 161 | MG-11 | 46 |
| 2-12 | M-12 | pUM12 | pMAH-12 | MGg-12 | 130 | MG-12 | 15 |
| 2-13 | M-13 | pUM13 | pMAH-13 | MGg-13 | 144 | MG-13 | 29 |
| 2-14 | M-14 | pUM14 | pMAH-14 | MGg-14 | 130 | MG-14 | 15 |
| 2-15 | M-15 | pUM15 | pMAH-15 | MGg-15 | 194 | MG-15 | 79 |
| 2-16 | M-16 | pUM16 | pMAH-16 | MGg-16 | 130 | MG-16 | 15 |
| 2-17 | M-17 | pUM17 | pMAH-17 | MGg-17 | 170 | MG-17 | 55 |
| 2-18 | M-18 | pUM18 | pMAH-18 | MGg-18 | 164 | MG-18 | 49 |
| 2-19 | M-19 | PUM19 | pMAH-19 | MGg-19 | 147 | MG-19 | 32 |
| 2-20 | M-20 | pUM20 | pMAH-20 | MGg-20 | 150 | MG-20 | 35 |
| 2-21 | M-21 | pUM21 | pMAH-21 | MGg-21 | 124 | MG-21 | 9 |
| 2-22 | M-22 | pUM22 | pMAH-22 | MGg-22 | 153 | MG-22 | 38 |

EXAMPLE 3

Harvest of polypeptide gene TM-1 containing pUM1 polypeptide in which *Mycoplasma gallisepticum* has been expressed in nature (1) Genomic Southern Hybridization of *Mycoplasma gallisepticum* using pUM1 insert DNA as a probe After 1 μg of *Mycoplasma gallisepticum* DNA obtained in Example 1 (1) was digested with restriction enzyme EcoR I, the digestion product was subjected to 0.6% low melting point agarose gel electrophoresis. After the electrophoresis, the gel was immersed in a denaturing solution (0.5 M NaOH, 1.5 M NaCl) for 10 minutes and further immersed in a neutralizing solution (3 M sodium acetate, pH 5.5) for 10 minutes to denature DNA. Following the neutralization, the DNA was transferred onto a nylon membrane in 6-fold SSC solution (0.7 M NaCl, 0.07 M sodium citrate, pH 7.5). After air drying, the membrane was heated at 80° C. for 2 hours. 4-Fold SET (0.6 M NaCl, 0.08 M Tris-HCl, 4 mM EDTA, pH 7.8), 10-fold Denhardt, 0.1% SDS, 0.1% $Na_4P_2O_7$, 50 μg/ml of denatured salmon sperm DNA and pUM1 insert DNA which had been labeled in a conventional manner were added to cause hybridization at 68° C. for 14 hours. The nylon membrane was overlaid on an X ray film. Autoradiography revealed that hybridization occurred on a fragment of about 1.7 kbp.

(2) Cloning of EcoR I-digested fragment of about 1.7 kbp into pUC18 and colony hybridization After 4 μg of *Mycoplasma gallisepticum* DNA obtained in Example 1 (1) was digested with restriction enzyme EcoR I, the digestion product was subjected to 0.6% low melting point agarose gel electrophoresis. After the electrophoresis, a fragment of about 1.7 kbp was recovered. The fragment was ligated by ligase with pUC18 cleaved through digestion with EcoR I and competent *E. coli* TG1 strain was transformed. The transformants were cultured at 37° C. for 15 hours in LB agar medium containing 0.003% of 5-bromo-4-chloro-3-indolyl-β-D-galactopyranoside, 0.03 mM of isopropylthio-β-D-galactopyranoside and 40 μg/ml of ampicillin. White colonies grown on the agar medium were transferred onto a nylon membrane followed by hybridization in a manner similar to (1). Autoradiography revealed that cloning was effected and, the plasmid was named pUMGT64.

(3) Determination of the entire base sequence of TM-1

The entire base sequence of TM-1 was analyzed in a manner similar to Example 1 (7) to determine the sequence. The entire base sequence is as shown in FIG. 2(a) and 2(b).

EXAMPLE 4

Figure 6:
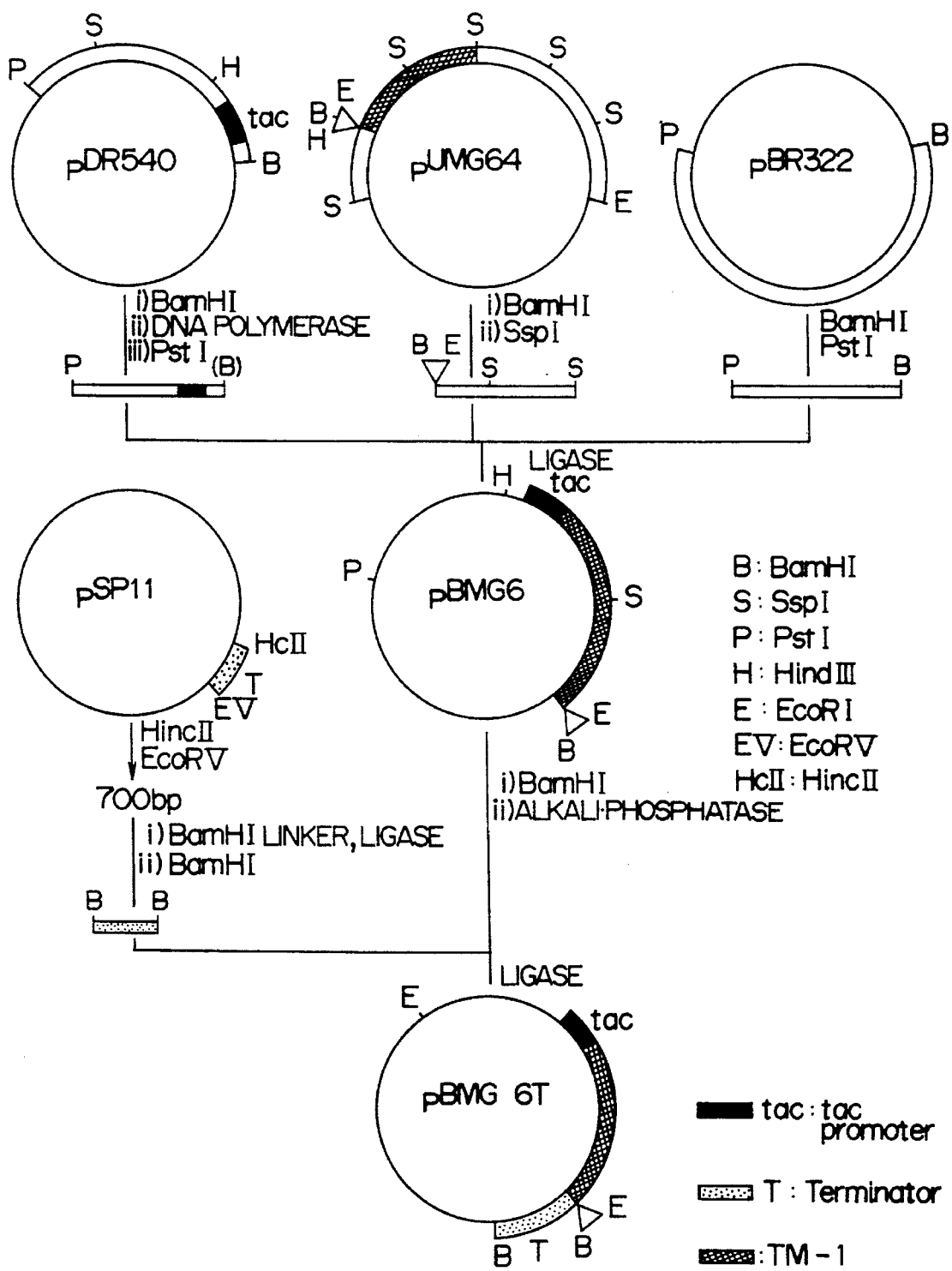

Production of expression plasmid pBMG6T of polypeptide TMG-1 encoded by TM-1 (FIG. 6)

Firstly, pDR540 was digested with restriction enzymes BamH I and Pst I; and the digestion product was then subjected to 0.8% low melting point agarose gel electrophoresis. A fragment was recovered from the gel. By treating with phenol-chloroform and precipitating with ethanol, a fragment of 1140 bp harboring tac promoter was recovered. Next, pUMGT64 obtained in (2) was fully digested with BamH I and then partially digested with restriction enzyme Ssp I. After 0.8% low melting point agarose gel electrophoresis, a fragment was recovered from the gel. By treating with phenol-chloroform and precipitating with ethanol, a fragment of about 840 bp containing TM-1 gene of the full length was recovered. On the other hand, pBR322 was digested with BamH I and Pst I. After 0.8% low melting point agarose gel electrophoresis, a fragment was recovered from the gel. By treating with phenol-chloroform and precipitating with ethanol, a fragment of 3240 bp was recovered. These 3 fragments were ligated with ligase and transformed competent *E. coli* TG1 strain. A plasmid was selected in a manner similar to Example 1 (6) and named pBMG6. This pBMG6 plasmid was cleaved with BamH I. By treating with phenol-chloroform and precipitating with ethanol, a fragment of 3240 bp was recovered. Next, 8 mer of BamH I linker was ligated with EcoR V-Hinc II fragment of about 700 bp containing the transcription termination sequence shown in Example 1 (8). By treating with phenol-chloroform and precipitating with ethanol, a DNA fragment was recovered. After the DNA fragment was digested with BamH I, the digestion product was subjected to 0.8% low melting point agarose gel electrophoresis. A fragment was recovered from the gel and treated with phenol-chloroform. By ethanol precipitation, a fragment of about 700 bp containing the transcription termination sequence was recovered. The cleaved pBMG6 and the fragment of about 700 bp were ligated with ligase. A plasmid was selected in a manner similar to Example 1 (6) and named pBMG6T.

EXAMPLE 5

Expression of TMG-1

After *E. coli* TG1 strain transformed with pBMG6T was cultured at 37° C. for 12 hours in LB medium containing 50 µg/ml ampicillin, 1 ml of the culture was collected and added to 100 ml of LB medium containing 50 µg/ml of ampicillin followed by culturing at 37° C. Two hours later, isopropylthio-β-D-galactopyranoside was so added as to show the concentration of 1 mM and culturing was continued at 37° C. for further 12 hours. After culturing, *E. coli* was centrifuged at 8,000 rpm for 10 minutes. After the cells were collected, the cells subjected to 10% SDS-PAGE and electrophoresed at 50 mA for 2 hours. After the electrophoresis, the gel was stained with Coomassie Brilliant Blue R-250 to newly detect a band of about 29 kilodaltons, amounting to about 10% of the total cell protein. Since this molecular weight of the protein is equal to the estimated value, said protein having about 29 kilodaltons is identified with the one encoded by TM-1 and named TMG-1.

EXAMPLE 6

Purification of TMG-1

After *E. coli* collected in Example 5 were suspended in 10 ml of PBS, the suspension was treated by freezing and thawing and then sonicated. Then, centrifugation was performed at 8,000 rpm for 10 minutes and the supernatant was recovered. The supernatant was subjected to ion exchange chromatography (Pharmacia Fine Chemicals Inc., FPLC anion exchange column MONO Q 10/10, 20 mM triethanolamine, pH 7.3, NaCl density gradient 0 M to 1 M [60 minutes], sample amount of 20 mg, flow rate of 4 ml/min, fraction size of 4 ml). From each of the collected fractions, 10 µl was adsorbed onto a nitrocellulose membrane. Immuno dot blotting (primary antibody; *Mycoplasma gallisepticum* infected chicken serum, secondary antibody;biotinated anti-chicken IgG rabbit serum, color forming system;chicken peroxidase complex, substrate;4-chloro-1-naphthol) was carried out, whereby TM-1 polypeptide could be detected around 0.6 M of NaCl concentration. The detected fraction was subjected to 8% SDS-PAGE and stained with Coomassie Brilliant Blue R-250. It was confirmed that about 90% of the total protein was TMG-1. By the procedures, about 200 μg of TMG-1 could be purified from the culture solution of TG1 transformed by pBMG6T.

EXAMPLE 7

Test on growth inhibition of *Mycoplasma gallisepticum*

Polypeptide MGg-1 encoded by pMAH1 which was obtained in a manner similar to Example 2 and TMG-1 obtained in Example 6 were respectively dissolved in Dulbecco's PBS buffer so that each shows the concentration of 500 μg/ml. Each solution, 1 ml, was subcutaneously injected to each Japanese white rabbit weighing about 2 kg, together with an equal volume of complete Freund adjuvant respectively. Further 4 weeks later, each of MGg-1 solution, 0.5 ml, and TMG-1 solution, 0.5 ml, described above was respectively administered to each rabbit subcutaneously as well as intravenously into the ear vein for the second immunization. Seven days later, it was confirmed in a conventional manner that antibody titer was increased and, anti-MGg-1 serum and anti-TMG-1 serum were collected from the ear artery of the rabbit.

On the other hand, *Mycoplasma gallisepticum* was liquid cultured by the method described in Example 1 (1). The culture solution, which color changed from red to yellow by a pH indicator, was diluted to 128-fold with medium for *Mycoplasma gallisepticum*. To 500 μl of the diluted culture solution was aseptically added 25 μl each of 6 samples: *Mycoplasma gallisepticum* infected chicken serum, the MGg-1 rabbit serum and anti-TMG-1 rabbit serum, standard rabbit serum and standard chicken serum which were quite free of antibody to *Mycoplasma gallisepticum* and medium for *Mycoplasma gallisepticum*. By culturing at 37° C., growth inhibition test was carried out.

On Days 0, 3 and 4 of the incubation, 10 μl each was collected from each of the culture solutions for growth inhibition test of *Mycoplasma gallisepticum*. Each of the collected culture solutions was spread on a plate of 1.2% agar medium for *Mycoplasma gallisepticum* followed by culturing at 37° C. in a 5% $CO_2$ incubator. The number of cells in the corresponding culture solution was deduced from the number of colonies of *Mycoplasma gallisepticum* formed, 7 days later. The results are shown in Table 2.

When the added sample was the culture solution of standard rabbit serum, standard chicken serum or medium, there was no difference in a proliferation rate of *Mycoplasma gallisepticum* and, the cell number reached the saturation on Day 3 of the incubation. In the culture solution added with anti-MGg-1 rabbit serum, anti-TMG-1 rabbit serum and infected chicken serum, proliferation of *Mycoplasma gallisepticum* was not proliferated at all up to Day 3. The results reveal that TMG-1 and fused proteins MGg-1 are antigens capable of inducing antibodies which effectively inhibit the growth of *Mycoplasma gallisepticum*.

TABLE 2

| Sample | Day 0* | Day 3 | Day 4 |
|---|---|---|---|
| Anti-MG-1 rabbit serum | $9.8 \times 10^3$ | $1.1 \times 10^4$ | $1.9 \times 10^4$ |
| Anti-TMG-1 rabbit serum | $9.8 \times 10^3$ | $1.0 \times 10^4$ | $9.0 \times 10^3$ |
| Standard rabbit serum | $9.8 \times 10^3$ | $2.8 \times 10^6$ | $3.3 \times 10^6$ |
| Infected chicken serum | $9.8 \times 10^3$ | $1.0 \times 10^4$ | $1.3 \times 10^4$ |
| Standard chicken serum | $9.8 \times 10^3$ | $2.9 \times 10^6$ | $3.2 \times 10^6$ |
| Culture medium | $9.8 \times 10^3$ | $3.0 \times 10^6$ | $3.2 \times 10^6$ |

*The day when the incubation was started.

Numerical values in the table indicate the number of cells in 1 ml of the culture solution.

EXAMPLE 8

*E. coli* transformed by pMAD1 was cultured in LB medium at 37° C. for 24 hours. The culture solution, 10 ml, was added to 1 l of LB medium charged in Sakaguchi flask followed by culturing at 37° C. for 2 hours. Isopropylthio-β-D-galactopyranoside was added thereto in a concentration of 1 mM followed by culturing for 24 hours. The culture solution was centrifuged at 5,000 rpm for 10 minutes while keeping at 2 to 5° C. After the precipitates were centrifuged and washed with phosphate buffered saline (pH 7.0) 3 times, 10 ml of phosphate buffered saline containing 0.01% of thimerosal was added to the precipitates. After sonication was performed for 30 seconds 5 times, the supernatant was collected and made crude antigen. To 10 volume of the crude antigen were added 10 volume of aluminum hydroxide gel containing 0.01% of thimerosal and 30 volume of sterilized phosphate buffered saline. The resulting mixture was made a vaccine.

The vaccine described above was intramuscularly inoculated to 3 SPF chickens at the age of 17 days in a dose of 0.5 ml. For supplemental immunization, the vaccine was intramuscularly inoculated at the age of 39 days. At the age of 66 days, agglutination reaction test of *Mycoplasma gallicepticum* and hemagglutination inhibition (HI) test were carried out to determine immune effect.

In the agglutination reaction test, 0.05 ml of Mycoplasma antigen manufactured by Nippon Pharmacy Co., Ltd. and 0.05 ml of vaccinized or non-vaccinized chicken serum were mixed on a glass plate and those forming a clear agglutination mass within 2 minutes were determined positive.

The HI test was performed by adding an equal volume of culture solution of 4 units of *Mycoplasma gallisepticum* S6 strain to each of diluted sera, mixing them, settling the mixture for 10 minutes to sufficiently sensitize and then adding blood cells thereto.

The results of the cell agglutination reaction test and HI test are shown in Table 3. The vaccinized chicken serum according to the present invention showed a markedly increased agglutination effect, indicating that the vaccine of the present invention exhibits highly immunizing effect.

TABLE 3

| Group | No. of Chickens | Agglutination Antibody Titer* | HI Antibody Titer |
|---|---|---|---|
| Vaccinized Group | 1 | +++ | <1:2 |
| | 2 | +++ | <1:2 |
| | 3 | – | <1:2 |
| Non-vaccinized Group | 4 | – | <1:2 |
| | 5 | – | <1:2 |

*–: negative
+++: strongly positive

EXAMPLE 9

Diagnosis of poultry Mycoplasma infection

Polypeptide obtained in Run No. (2-1) of Example 2 and TMG-1 obtained in Example 6 were dissolved in bicarbonate buffer (15 mM $Na_2CO_3$, 35 mM $NaHCO_3$), respectively, in concentrations of 10 to 100 μg/ml.

On the other hand, bicarbonate buffer in which 50 μl/well of the polypeptide had been dissolved was charged in a 96 well microtiter plate. After allowing to stand at 4° C. overnight, incubation was carried out at 37° C. for an hour to immobilize. After the immobilization, the plate was washed 5 times with 1% bovine serum albumin-containing PBS. To each well of the microtiter plate was added 100 μl each of sera collected from chickens infected with *Mycoplasma gallisepticum* as a positive control and sera collected from test chickens. Then incubation was performed at 37° C. for an hour. Each well was washed 5 times with PBS. A 1000-fold diluted solution of rabbit IgG which bound horse radish peroxidase to chicken IgG was added to each well in an amount of 100 μl each per well followed by incubation at 37° C. for an hour. After again washing with PBS 5 times, 2,2'-azino-di-[3-ethyl-benzthiazoline sulfonate] which was substrate of horse radish peroxidase was added followed by incubation at 37° C. for 30 minutes. Absorbance was measured at a wavelength of 405 nm using an immunoreader. As the result, only the serum collected from the chicken infected with *Mycoplasma gallisepticum* selectively absorbed the wavelength of 405 nm. The results reveal that the polypeptide can be utilized as a poultry diagnostic for *Mycoplasma gallisepticum* infection.

What is claimed is:

1. An isolated and purified polypeptide which reacts with anti-*Mycoplasma gallisepticum* chicken sera through an antigen-antibody reaction, wherein said polypeptide is selected from the group consisting of MG-1, MG-2, MG-3, MG-7, MG-8, MG-9 and TMG-1.

2. The polypeptide according to claim 1, wherein said polypeptide has an amino acid sequence as shown in any of FIGS. 1(*a*) to 1(*f*).

3. The polypeptide according to claim 2, wherein said polypeptide has an amino acid sequence as shown in FIG. 1(*a*).

4. The polypeptide according to claim 1, wherein said polypeptide has an amino acid sequence as shown in FIG. 2.

5. An isolated and purified polypeptide which reacts with anti-*Mycoplasma gallisepticum* chicken sera through an antigen-antibody reaction, wherein said polypeptide is TMG-1 and wherein said polypeptide has an amino acid sequence as shown in FIG. 2.

6. A fused protein whose C-terminus is a polypeptide which reacts with anti-*Mycoplasma gallisepticum* chicken sera through an antigen-antibody reaction, wherein said polypeptide is selected from the group consisting of MG-1, MG-2, MG-3, MG-7, MG-8, MG-9 and TMG-1; and whose N-terminus is an enzyme protein derived from bacteria.

7. A fused protein according to claim 6, wherein said enzyme protein derived from bacteria is β-galactosidase or β-lactamase.

8. A fused protein whose C-terminus is a polypeptide which reacts with anti-*Mycoplasma gallisepticum* chicken sera through an antigen-antibody reaction, wherein said polypeptide is TMG-1 and wherein said polypeptide has an amino acid sequence as shown in FIG. 2; and whose N-terminus is an enzyme protein derived from bacteria.

9. A fused protein according to claim 8, wherein said enzyme protein derived from bacteria is β-galactosidase or β-lactamase.

* * * * *